(12) United States Patent
Gugger et al.

(10) Patent No.: US 6,565,912 B1
(45) Date of Patent: May 20, 2003

(54) PRODUCTION OF ISOFLAVONE ENRICHED FRACTIONS FROM SOY PROTEIN EXTRACTS

(75) Inventors: Eric Gugger, Decatur, IL (US); Richard Grabiel, Decatur, IL (US)

(73) Assignee: Archer-Daniels-Midland, Decatur, IL (US)

( * ) Notice: Subject to any disclaimer, the term of this patent is extended or adjusted under 35 U.S.C. 154(b) by 0 days.

(21) Appl. No.: 09/697,696

(22) Filed: Oct. 26, 2000

Related U.S. Application Data (60) Continuation-in-part of application No. 09/478,751, filed on Jan. 6, 2000, now Pat. No. 6,171,638, which is a continuation-in-part of application No. 09/035,588, filed on Mar. 5, 1998, now Pat. No. 6,033,714, which is a continuation-in-part of application No. 08/868,629, filed on Jun. 4, 1997, now Pat. No. 5,792,503, which is a division of application No. 08/614,545, filed on Mar. 13, 1996, now Pat. No. 5,702,752.

(51) Int. Cl.[7] .................................................. A23L 1/20
(52) U.S. Cl. ........................ 426/634; 426/425; 426/431; 426/429; 426/443; 426/478; 426/490; 426/520
(58) Field of Search ................................ 426/634, 425, 426/431, 429, 443, 478, 490, 520

(56) References Cited

U.S. PATENT DOCUMENTS

| | | | | |
|---|---|---|---|---|
| 4,428,876 A | * | 1/1984 | Iwamura | |
| 5,702,752 A | * | 12/1997 | Gugger et al. | |
| 5,792,503 A | * | 8/1998 | Gugger et al. | |
| 6,033,714 A | * | 3/2000 | Gugger et al. | |
| 6,171,638 B1 | * | 1/2001 | Gugger et al. | |

* cited by examiner

*Primary Examiner*—Anthony J. Weier
(74) *Attorney, Agent, or Firm*—Sterne, Kessler, Goldstein & Fox, PLLC (57) ABSTRACT

The temperature sensitive differential of solubilities of various isoflavone fractions is used to initially separate the fractions, preferably by heating an aqueous soy molasses or soy whey feed stream. The temperature of the feed stream is selected according to the temperature at which a desired isoflavone fraction or fractions become soluble. Then, the heated feed stream is passed through an ultrafiltration membrane in order to concentrate the isoflavones. The feed stream is put through a resin adsorption process. The isoflavone fractions are treated with either reverse osmosis or ultrafiltration (or both) to complete a solvent removal and to achieve a higher isoflavone concentration in the end product. Then, the feed stream is dried, preferably by spray drying, to produce dry particles.

39 Claims, 4 Drawing Sheets

PRODUCTION OF ISOFLAVONE ENRICHED FRACTIONS FROM SOY PROTEIN EXTRACTS

This is a continuation-in-part of Ser. No. 09/478,751 filed Jan. 6, 2000, now U.S. Pat. No. 6,171,638 which in turn is a continuation-in-part of Ser. No. 09/035,588, filed Mar. 5, 1998, now U.S. Pat. No. 6,033,714, which in turn is a continuation-in-part of Ser. No. 08/868,629, filed Jun. 4, 1997, now U.S. Pat. No. 5,792,503, which in turn is a division of Ser. No. 08/614,545, filed Mar. 13, 1996, now U.S. Pat. No. 5,702,752.

The invention relates to processes for producing isoflavone fractions by a treatment of an aqueous alcohol extract of defatted soybean flakes.

BACKGROUND OF THE INVENTION

This invention will find use when processing any one of a number of plants or plant material, the preferred one of which is the soybean.

Those who are skilled in the art will readily perceive a variety of other plants or plant material which may be used, for example, red clover, kudzu, alfalfa, tea, cocoa, and subterranean clover are also expected to work in this invention. Accordingly, the terms plant, plant material, vegetable matter, and vegetable are to be construed herein as including these and other suitable materials.

As used herein, the term "isoflavone" is a flavonoid and includes saponins, lignans, alkaloids, catechins, and phenolic acids and also includes malonyl, acetyl, glucoside, and aglycone forms of the isoflavones.

For some background information on processing soy, reference may be made to the following articles: "*Isolated Soy Protein*" by C. W. Kolar, S. H. Richert, C. D. Decker, F. H. Steinke, and R. J. VanderZanden, found as chapter VIII of *New Protein Foods*, Vol. 5, eds. Aaron M. Altschul and Harold L. Wilcke, Academic Press, Inc. 1985; "*Traditional Soyfoods: Processing and Production*" by Peter Goldbitz; and "*Soy Protein Products: Processing and Use*" by Edmund W. Lusas and Mian N. Raz, both (0022-3166/95) published 1995 by the American Institute of Nutrition. A process for producing soy whey is disclosed on pages 386, 387 of "*Soybeans Chemistry, Technology, and Utilization*" by KeShun Liu, published by Chapman & Hall, 115 Fifth Avenue, New York, N.Y. 10003.

Isoflavones are a unique class of plant flavonoids that have a limited distribution in the plant kingdom and may be physically described as colorless, crystalline phenolic ketones. The most common and important dietary source of these isoflavones are soybeans which contain the following twelve isoflavone isomers: genistein, genistin, 6"-0-malonylgenistin, 6"-0-acetylgenistin; daidzein, daidzin, 6"-0-malonyldaidzin, 6"-0-acetylgenistin; glycitein, glycitin, 6"-0-malonylglycitin, 6"-0-acetylglycitin (Kudou, Agric. Biol. Chem. 1991, 55, 2227–2233). Ninety-seven to ninety-eight percent of the soybean isoflavones are in the glycosylated form.

Traditionally, individuals have been limited in their use of soy foods to increase their levels of dietary isoflavones because the number and variety of soy foods is limited especially in the U.S. marketplace. Also, natural flavors and color of some soy products have been described by some people as being bitter and unappetizing.

The isoflavone, genistin, was first isolated from soybean meal in 1931 by Walz (Justus Liebigs Ann. Chem 489, 118) and later confirmed in 1941 by Walter (J. Amer. Chem. Soc. 63, 3273). Patents have described the production of isoflavone enriched soy-protein products (WO 95/10512; WO95/10529; WO 95/10530), genistin malonate and daidzin malonate (U.S. Pat. No. 5,141,746), pharmaceutical-type compositions containing isoflavones (U.S. Pat. Nos. 5,424,331; 4,883,788), and isolation and modification of isoflavones from tempeh (U.S. Pat. Nos. 4,390,559; 4,366,248; 4,366,082; 4,264,509; 4,232,122; 4,157,984). The present invention relates to the manufacture of highly enriched isoflavone products containing either a wide-range of soy isoflavones or highly-purified genistin gained from an ethanol extract of defatted soybean flakes.

For example, coronary heart disease (CHD) is a leading cause of death, especially in the United States and other industrialized nations. Elevated total and low density lipoprotein (LDL) cholesterol levels are important risk factors for CHD. In humans, soy protein products appear to lower serum total cholesterol levels by an average of about 9.3% and to lower low-density lipoprotein (LDL) cholesterol by an average of about 12.9% when consumed at an average intake level of 47 g soy protein per day (Anderson et al., *NEJM*, 333: 276–282, 1995).

Isoflavones (phytoestrogens) are implicated as a class of compounds in soy protein products which is at least partly responsible for this cholesterol-lowering effect in animals (Setchell, in McLachlan JA, ed., Estrogens in the Environment II: 69–85, 1985). In addition, studies with primates suggest that soy isoflavones may account for up to about 60–70% of the hypocholesterolemic properties of soy protein (Anthony et al., Circulation, 90: Suppl: I-235. (abstract), 1994; Anthony et al., J. Nutr., 125: Suppl 3S: 803S–804S. (abstract), 1995; Anthony et al., Circulation, 91: 925. (abstract), 1995).

It has also been suggested that isoflavones have an ability to play a role in the prevention of certain cancers. Japanese women who have consumed diets rich in isoflavones appear to have a very low incidence of breast cancer (Adlercreutz et al., J. Nutr. 125: 757S–770S, 1995). Soy products have also been shown to decrease mammary tumor formation or to inhibit mammary tumor progression in rat breast cancer models (Barnes et al., Clin. Biol. Res. 347: 239–253; Hawrylewicz et al., J. Nutr. 121: 1693–1698, 1991). Genistein has been shown to inhibit protein tyrosine kinase (Akiyama et al., J. Biol. Chem. 262: 5592–5595, 1987), to inhibit angiogenesis (Fotsis et al., Proc. Natl. Acad. Sci. USA 90: 2690–2694, 1993), and to induce differentiation in several malignant cell lines (Peterson, J. Nutr. 125: 784S–789S, 1995), all of which may be important risk factors in cancer development. Genistein and Biochanin A also appear to inhibit the growth of androgen-dependent and independent prostatic cancer cells in vitro (Peterson and Barnes, Prostate 22: 335–345, 1993). Genistein may act as an antioxidant (Wei et al., Nutr. Cancer 20: 1–12, 1993).

Beyond cancer, it is thought that at least some of the soy isoflavone fractions are especially beneficial for women in general since it is a source of plant or vegetable estrogen. It is thought that plant or vegetable estrogen provides many of the advantages and avoids some of the alleged disadvantages of animal estrogen. Hence, it is especially desirable to enable the isoflavone fractions to be used in a wide variety of ways, such as in beverages and foods including health bars. This means that the isoflavone fractions should not introduce unacceptable tastes or unappetizing colors.

Some of these medical conditions may be either preventable or treatable by a use of phytochemicals, especially isoflavones, as a source of supplemental hormones. Hence, proper diet should contain the desired phytochemicals.

It is also thought that there are superior results when a plurality of such phytochemicals are consumed in proper combinations. However, a trouble is that many people do not have or do not like the proper kind of diet which provides the desirable effects. Therefore, the problem is to furnish the necessary food values in some other form. Accordingly, it is desirable to provide a refinement process which is able to provide a selected combination of phytochemicals tailored to a specific symptom.

The process described in U.S. Pat. Nos 5,702,752; 6,017,555; and 6,033,714 produce an excellent concentration of isoflavones. However, the end product could be improved and produced at lower cost especially by reducing the energy required to dry an aqueous feed stream carrying the isoflavone fractions. Also, it is desirable to increase the concentration of the isoflavone fraction in the end product. Isoflavones are preferably formed into pills, tablets, capsules, liquids, and food ingredients which may be ingested without having to taste the original food product. Also, there are times when it is desirable to use the isoflavones as supplements in foods, beverages, medical foods, health bars, and certain other dietary supplement products.

SUMMARY OF THE INVENTION

Accordingly, an object of this invention is to provide a combination of isoflavone fractions which have a neutral color and a bland flavor, and which together provide a profile especially directed to specific health problems. In particular, an object is to provide a supplement which may be included in a great variety of foods and beverages. More particularly, an object is to provide isoflavone materials of greater concentration where smaller quantities of a supplement deliver the same amount or more of the desired isoflavones.

Another object is to provide a process that uses soy whey, which has sometimes been an unacceptable starting material for use in more important and valuable products; therefore, it is often generated as a by-product of soy processing.

A still further object of the invention is to provide a process that results in an intermediate product that can be conveniently stored for later processing into a pure form when required. Another object is to provide a process that requires less equipment and less time to produce a more consistently pure product at a lower cost, especially a product with a greater concentration of isoflavones.

In keeping with an aspect of the invention, a product resulting from a removal of alcohol from an aqueous alcohol feed stream of vegetable material containing at least two isoflavone fractions is treated with either reverse osmosis or ultrafiltration (or both) in order to achieve a higher concentration of isoflavone solids in the end product. This process of reverse osmosis or ultrafiltration (or both) prior to drying to a dry product reduces the amount of evaporation as compared to the former process in order to produce a significant reduction in energy demand, and therefore, the cost of the process. Then, the feed stream is dried to a dry product, such as powder, preferably by spray drying. Optional steps including redissolving the dry product, concentrating the redissolved product, separating and redrying the crystals. As a result, the isoflavone concentration in the product before spray drying is 1%–10% solids and preferably 4%–7% solids.

In keeping with other aspects of the invention, these and other objects are accomplished by starting preferably with soy molasses, or alternatively with soy whey, which is subjected to ultra-filtration in order to produce a permeate which then passes through a column containing an adsorbing resin. The resin is then washed with water and eluted with aqueous alcohol, preferably ethanol. In the Assignee's previous patent, the next step evaporates alcohol until the solids are in the range of approximately 1–20% of the remaining liquid. This was a step with a rather high energy demand. The resulting product is dried, preferably by spray drying or by another appropriate means. The dried product may then optionally be stored, or may be immediately further processed by adding a solvent, preferably water, to dissolve the soluble fraction of the dried product, which is enriched in the undesirable color and flavor fractions. The non-soluble fraction, which is enriched in isoflavones, can then be separated from the soluble fraction by any conventional means, and dried preferably by spray drying.

In keeping with a still further aspect of the invention and in order to fine tune the characteristics of the product, the product is dried to a powder. Then, a plurality of lots may be blended together to achieve a standard isoflavone level. When the product is ready for use as, for example, in a food ingredient or the like, the blended product may be rehydrated.

There are many advantages resulting from the process of drying, adding an ingredient, blending, and then rehydrating since it permits storage in a dry form, better blending, and closer control over the specifications of the final product. It is easier to control product specifications by a blending of optimally selected dry ingredients. Also, dry storage smoothes production and enables sudden large orders to be filled quickly. Thus, quality control is made easier.

In addition, there is less equipment usage since it is no longer necessary to have large batches of product sitting in expensive tanks over long periods of time (often as much as two days) during which crystals are separated from their mother liquid. Since the product may be held in storage in a dry form, there is a less likelihood that contamination might occur. There is a larger commercial market for dry powder than there is for a liquid product. The dry product better enables a final usage in many forms such as pills, liquids, health bars, ingredients for various foods, and the like.

BRIEF DESCRIPTION OF DRAWINGS

These and other objects of this invention will become more apparent from the following specification taken with the attached drawings, in which.

DETAILED DESCRIPTION OF THE INVENTION

The invention begins with a product (such as protein isolate, soy molasses, or soy solids) which is usually thought of as an end product. The protein isolate, which is normally considered an end product, may be 90% wt. or more protein. Soy molasses or soy solids are called "concentrate" and are about 60% protein. Then, a further refinement converts that product into a combination of selected isoflavones having a profile designed to address certain health needs. After the inventive further refinement, 5–90% wt. of the combination is isoflavones. With optional steps of drying, redissolving the dried product, crystalizing the redissolved product, and redrying, the concentration of isoflavones in the end product can be raised to 70–90% wt. Protein is only a very minor part of the remainder.

Figure 1:
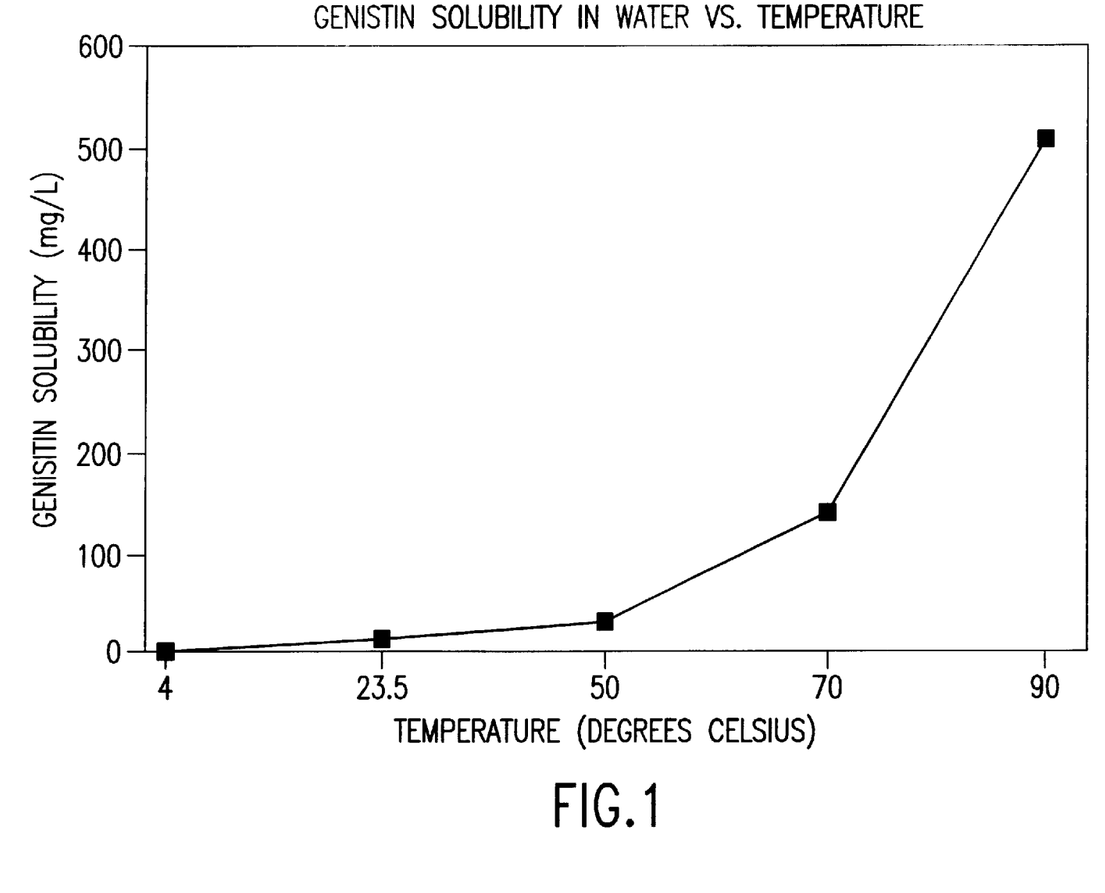
FIG. 1 is a graph showing the solubility of genistin in water vs. temperature.

In greater detail, this invention employs methods based on the differential solubilities of isoflavones in aqueous solutions. Genistin is the least water soluble of the isoflavone glycosides, is insoluble in cold water, and is only slightly soluble in hot water. FIG. 1 shows that the solubility of genistin is practically unchanged as the temperature increases from 4° C. to 50° C., but that the solubility increases rapidly as the temperature increases from 70° to 90° C. Therefore, if the manufacturing process is to recover genistin, the recovery step should be carried out at the high temperature end of the scale.

All isoflavone glycosides other than genistin have higher solubilities in water and readily pass through an ultrafiltration membrane, along with other water soluble components. By increasing the temperature of the aqueous solution prior to ultrafiltration, genistin and all other isoflavones can be separated from insoluble materials. The isoflavones in the ultrafiltration permeate can be recovered by treating the solution with a resin, washing the resin with water to remove soluble sugars, and eluting the isoflavones with a mixture of ethanol and water, followed by drying.

The starting material for the inventive processes is derived from an aqueous ethanol extract of hexane-defatted soybean flakes. The defatted soybean flakes are extracted with aqueous ethanol (approximately 60–80% ethanol by volume) at temperatures in the range of about 44°–63° C. or 120°150° F. This aqueous ethanol extract is then subjected to a vacuum distillation in order to remove ethanol. The alcohol-stripped extract is also known as "soy molasses" or "soy solubles." Soy molasses is a by-product of processes which make soy protein concentrate.

An alternative starting material is soy whey. The whey may be made in any of many well-known ways, one of which is shown on page 387 of the above-cited book "Soybeans" by KeShun Liu. In general, this Liu process begins with defatted soy meal which is passed through an aqueous extraction of pH 9.0. Then, the aqueous material is centrifuged followed by an isoelectric precipitation at a pH 4.5. The resulting material is separated into curd and whey. The curd is further processed into soy protein isolate.

Then the extract (either molasses or whey) is adjusted within an appropriate temperature range (about 65–95° C.) and subjected to ultrafiltration preferably by using a 100,000 molecular weight cut-off (MWCO) membrane. However, the process is not limited to this 100,000 cut-off membrane since any membrane or ceramic element which enables a filtration of the desired isoflavones may be used, such as a membrane in the range of 600–1,000,000 molecular weight cut-off. The smallest cut-off membrane suitable for the inventive procedures should pass a molecular weight of 532, which provides a sufficient retention of insoluble material and passage of isoflavones. Moreover, ultrafiltration may be performed on the basis of size, rather than molecular weight. Size, of course, often correlates roughly with molecular weight. An 0.1 micron membrane is another preferred membrane.

Figure 2:
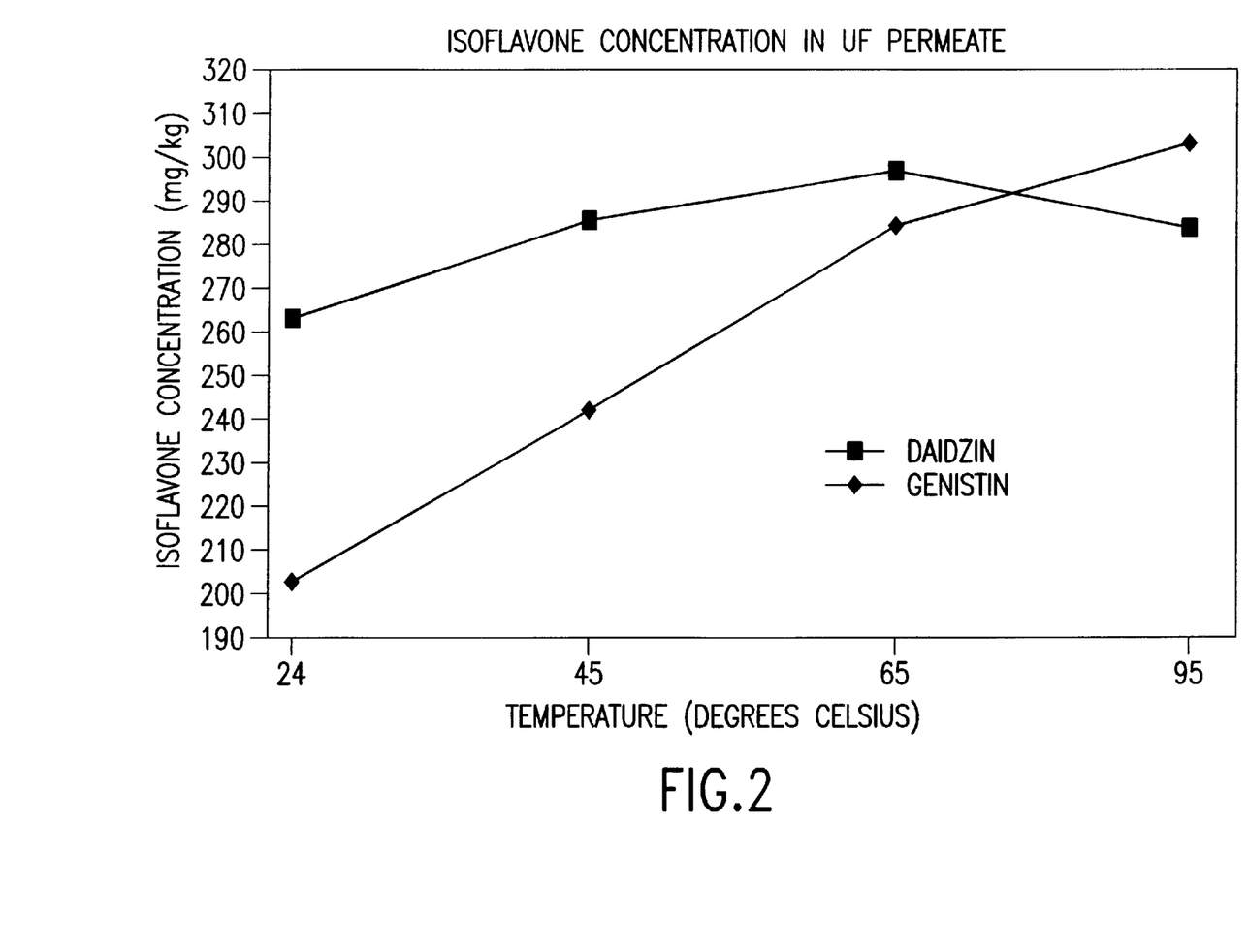
FIG. 2 is a graph showing the concentration of isoflavone in a UF permeate vs. temperature.

The effect of temperature on the concentration of two principal isoflavones, daidzin and genistin, in the UF permeate, is shown in FIG. 2. Cooler temperatures result in lower concentrations of genistin in the UF permeate. Daidzin concentrations are much less affected by temperature. To achieve optimal concentrations of isoflavones in the UF permeate, ultrafiltration should be carried out at a temperature above 65° C.

For example, FIG. 2 shows the differential between the concentration of daidzin and genistin in an aqueous solution permeate subjected to ultrafiltration. Ultrafiltration at 24° C. produces a high concentration of daidzin and a low concentration of genistin. Therefore, if the manufacturing step is to recover daidzin and reject genistin, perhaps the recovery should be carried out at the relatively low temperature of 24° C., although the exact temperature may be selected on a basis of how much genistin can be located in the permeate. On the other hand, if the manufacturing process is designed to recover both daidzin and genistin, perhaps it would be better to operate at the crossover point of about 78° C. For genistin, recovery should be carried out at a higher temperature.

Figure 3:
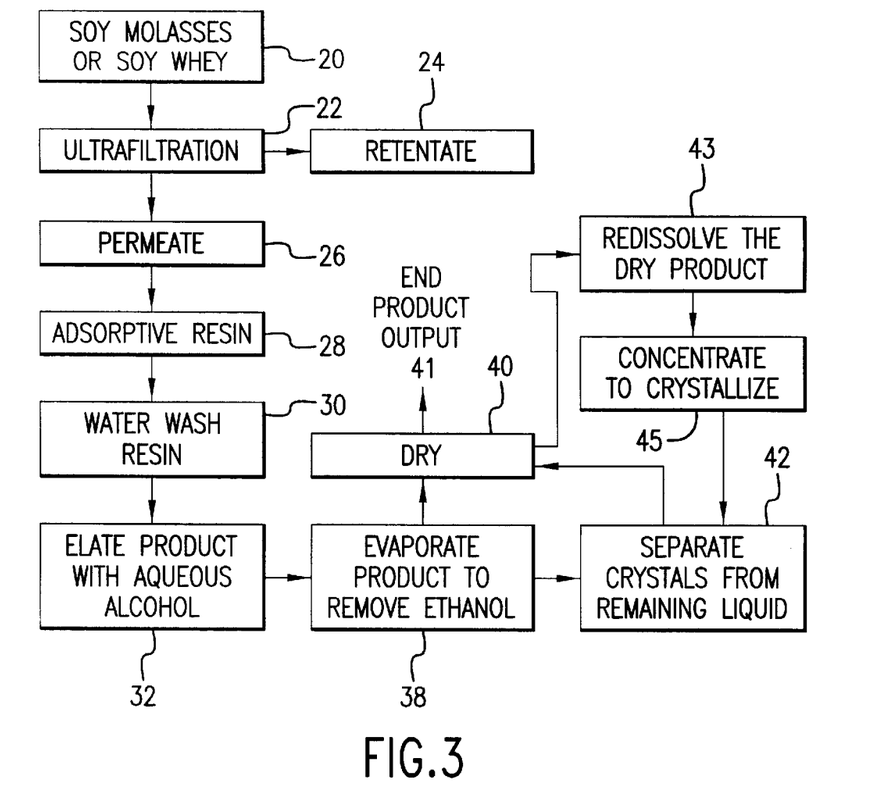
FIG. 3 is a process flow diagram showing the production of the inventive product.

A flow diagram representing one example of a manufacturing processes is shown in FIG. 3.

In greater detail, FIG. 3 shows at 20 that the preferred plant or vegetable starting material is either soy molasses or soy whey which is subjected to ultrafiltration at 22. At 24, the retentate of the ultrafiltration is further processed, recycled, or otherwise used in another process.

If a batch type process is employed, the volume of the UF retentate fraction 24 is reduced during the ultrafiltration process by about one-third to two-thirds of the original alcohol-stripped extract volume, or stated otherwise is up to 12–15% solids. The UF retentate may be diafiltered with about one to three retentate volumes of water, which has been previously adjusted to be within a temperature range of about 65–95° C. in order to recover a greater percentage of isoflavones in the permeate. The retentate will then be used in some other process having no direct relationship with the process shown in FIG. 3.

Figure 4:
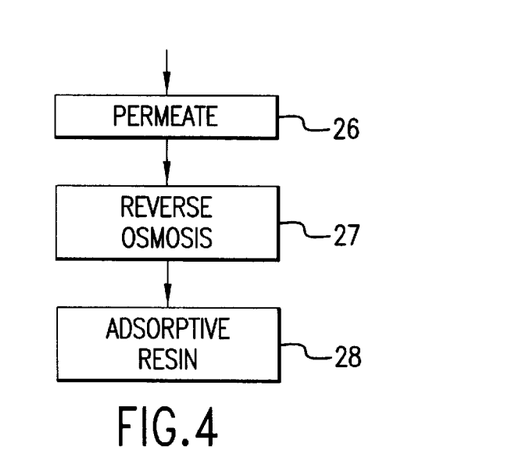
FIG. 4 is a fragment of FIG. 3 including a reverse osmosis step.

With or without the diafiltered permeate, the ultrafiltration permeate at 26 contains a variety of isoflavones and is adjusted to an appropriate temperature (45–95° C.). Then, it is treated with an adsorptive resin at 28 in either a batch or, preferably, chromatography column type process. As shown in FIG. 4, in some examples, a reverse osmosis step 27 may be included between the permeate step 26 and the adsorptive step 28.

More preferably, a continuous process is designed to use a plurality of chromatography columns wherein one column is loading while another column is eluting with still other columns in various stages between loading and eluting. This way, there may be a continuously flowing stream of finished product. There are a number or resins which may be used in the chromatography column. The resin may be, but is not limited to, ethylvinylbenzene-divinyl-benzene, styrene-divinyl-benzene or polystyrene polymers or copolymers, and may be either ionic or non-ionic.

A particularly attractive resin for use in the inventive process is "Amberlite" XAD-4 polymeric adsorbent sold by the Rohm and Haas Company at the Independence Mall West, Philadelphia, Pa. 19105. The manufacturer describes this resin as a non-ionic polymeric adsorbent supplied as insoluble white, cross-linked polymer beads which derives its adsorptive properties from its macroreticular structure containing both a continuous polymer phase and a continuous pore phase. This structure gives this polymeric adsorbent excellent physical, chemical, and thermal stability.

"Amberlite" XAD-4 polymeric adsorbent is further described as capable of being used through repeated cycles, in columns or batch modes, to adsorb hydrophobic molecules from polar solvents or volatile organic compounds from vapor streams. Its characteristic pore size distribution is said to make "Amberlite" XAD-4 polymeric adsorbent a choice for the adsorption of organic substances of relatively low molecular weight.

The physical properties of "Amberlite" XAD-4 are described by this manufacturer as follows:

| | |
|---|---|
| Matrix | Macroreticular cross-linked aromatic polymer |
| Appearance | White translucent beads |
| Particle Size | 0.3–1.2 mm (90% within) |
| True Wet Density | 1.02 g/ml |
| Surface Area | 800 m$^2$/g minimum |
| Porosity | 55% (vol/vol) minimum |
| Pore Size Range | 1–150A |

Following passage through the chromatography columns, the resin is washed with water at 30. Next, the isoflavones are eluted at 32 with an aqueous alcohol such as ethanol, methanol, or isopropanol (20–100% by volume, at 25–85° C.) as either a gradient or single percentage process. Here, 80% ethanol is preferred at a temperature of 40–70° C.

At 38, the resulting material is evaporated to provide a liquid having about 1–20% dry solid material in order to begin crystallization by removing the alcohol used in step 32. The evaporated product may then be further processed by spray drying at 40. The resulting dried material is approximately reddish-brown and approximately 20–60% isoflavones on a solids basis. It is thought that the most usual range for such dried material produced from soy molasses is about 30–50% isoflavones and from soy whey is about 20–40% isoflavones which seems to depend on the isoflavone concentration in the starting material, feed loading, and other variables. Or, further processing may be carried out by adjusting the evaporated product to an appropriate temperature (4–45° C.) to promote crystallization of isoflavone fractions.

These crystals can then be separated by settling, decanting, centrifuging, or filtering crystals at 42, to produce the resulting product which is cream colored, bland tasting, and about 50–90% isoflavones upon drying. It is thought that decanting, centrifugal filtration or using Hydroclone® machinery available from Dorr-Oliver in Milford, Connecticut will also work for such separation. When produced from soy molasses, the resulting crystalline product is most usually 80–90% isoflavones and when produced from soy whey, is most usually 55–70% isoflavones.

Means are provided for increasing the concentration of isoflavones by adding a loop which includes the steps of redissolving the dry powder, crystallizing the redissolved material, separating the crystals from the liquid, and then again drying the separated crystals. More particularly, the product at step 38 may receive any of several different treatments depending upon the desired end product 41. One process may take the final end product output 41 directly from the product evaporated at 38 through the drying at step 40. Another process may send the product evaporated at 38 through a crystallization and separation of crystals from liquid at step 42 through drying at step 40 to the end product output 41.

A preferred process produces a highly concentrated output product which involves processing the product in the loop 38, 40, 43, 45, 42, and 40 (FIG. 3) to become the highly concentrated end product which is about 70–90% wt. isoflavones at output 41. In greater detail, the evaporated product 38 is dried to a powder at 40. Then it is sent to step 43 where the dry product is redissolved. Next, the redissolved product is sent to a crystallizer 45 where the resulting crystals become a highly concentrated form. Then, the crystals are separated from liquid at 42, and are sent to the dryer at 40 to redry the highly concentrated form, which becomes the end product at 41.

The concept of crystallizing, drying, redissolving, recrystallizing and redrying may be expanded, as may be desired, to further concentrate the end product 41 by recirculating the isoflavone material through the closed loop involving steps 40, 43, 45, 42, and 40.

Figure 5:
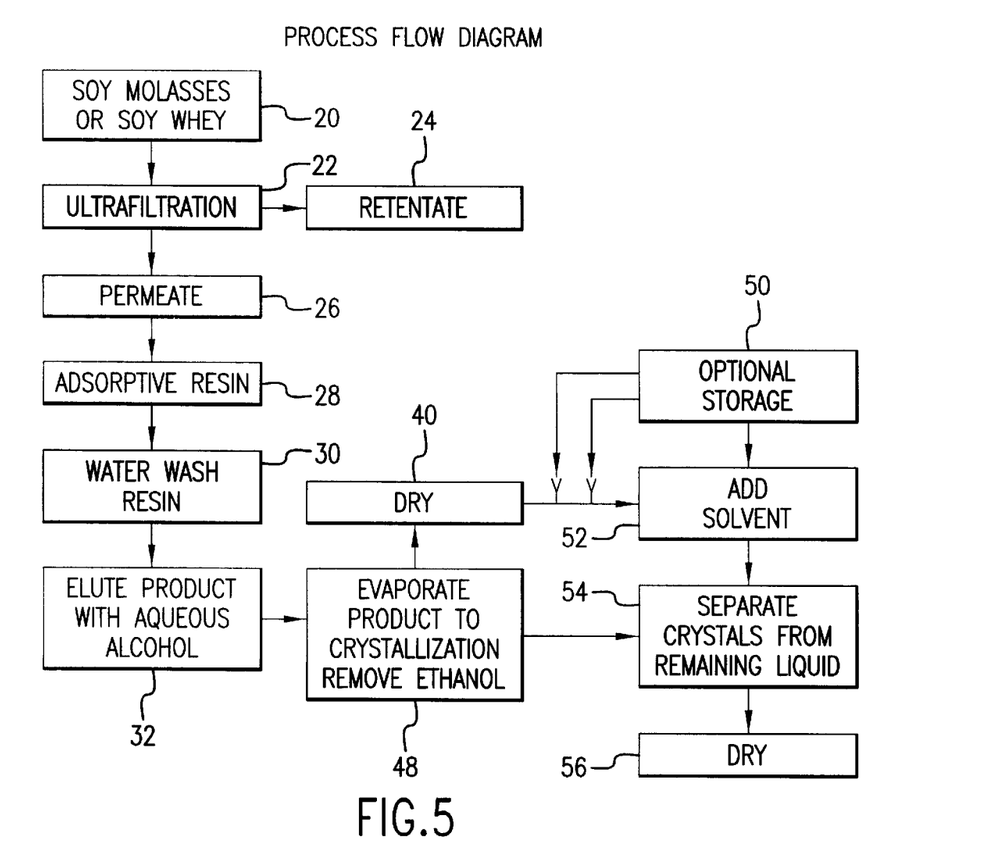
FIG. 5 is a process flow diagram showing a new method of production of the inventive product.

Another flow diagram representing one example of an improved manufacturing process is shown in FIG. 5, where the product is dried for storage, blending, etc., and then rehydrated for its end use. FIG. 5 shows a process which is the same as the process shown in FIG. 3, from step 20 through step 32. Therefore, these steps will not be explained again.

Briefly, a fine-tuning step is taken in which higher concentrations of isoflavones may be achieved while eliminating much of the evaporation step at 48. More specifically, reverse osmosis and ultrafiltration is performed at 49 after the isoflavones are eluted with an aqueous alcohol in the adsorptive resin at step 32 and the alcohol is driven off at 48. After the alcohol is so removed, the initial solids concentration is less than about 1%. The fine-tuning step resides in the treatment taken prior to the drying step 40, which may be spray drying, for example.

In greater detail, at step 48, the product stream is evaporated somewhat to remove ethanol and promote crystallization of the isoflavones. This is the step where a previously high energy demand occurred because complete evaporation was required which the subject invention has reduced by greatly reducing the amount of heat that is required for complete evaporation. The product stream from step 48 is preferably treated with reverse osmosis and then possibly with ultrafiltration, although either of these treatments may be taken alone. The ultrafiltration preferably uses a 10,000 to 100,000 molecular weight cut-off membrane. Either a reverse osmosis or an ultrafiltration 49, or both increase the solids content of the stream to reduce the energy needed for complete drying. The complete drying by evaporation requires much more energy than the topping off drying after reverse osmosis or ultrafiltering.

The reverse osmosis or ultrafiltration at step 49 starts with a stream having a solids concentration of less than 1%. These treatments may result in a more concentrated product having a solids content of 1% to 10%, and optimally in the range of 4% to 7% solids by weight. A cooling of the product helps to promote crystal formation. Preferably, the cooling is simply allowed to occur over time to reach ambient temperature or any of several known methods may be used to reduce the temperatures of this liquid product.

Ultrafiltration will result in a solids concentration of 1% to 60%, or optimally between 15% and 30%. This means of concentration can then be used to produce yet a higher solids concentration of about 70% isoflavones. Because it is done at a lower temperature, isoflavones are crystallized, while water-soluble components such as saponins, phenolic acid, and maltols, are left in solution and may be removed via ultrafiltration.

Then, the output of the reverse osmosis or ultrafiltration is fed into any suitable dryer 40 (such as a spray dryer, for example) where the crystals produced in step 32 or 49 are reduced to a dry powder. Depending upon the needs of any particular production run, the dry powder may be stored at 50.

This treated product may then be resolubilized and or further filtered to produce an isoflavone product of a quality similar to that achieved by spray drying alone, but with the benefit of significant reduction in the energy demand of evaporating a liquid of less than 1% solids. Alternatively, the treated product may be filtered or filtered and washed to produce a purer isoflavone product of up to 100% pure. Higher concentrations of isoflavones result in a product with less color and off flavor which makes this product more suitable as a food additive, as well as lowering the amount of solids necessary to deliver a given amount of isoflavones.

When the time comes to further continue the process, the powders extracted from either the dryer 40 or the optional storage 50 are treated with a suitable solvent at 52. This solvent preferentially dissolves the colors and flavors, while the isoflavones remain preferentially undissolved, allowing for an relatively inexpensive further purification of the isoflavones. The solvent is preferably selected from the group of tap water, deionized water, distilled water, ethanol, isopropanol, methanol, and combinations of these solvents. In the preferred form, water is used. In the most preferred form, tap water is used. Step 52 works at a range of temperatures, from at least about 4° C. to at least about 95° C., and the preferred range is about 10–70° C., with the more preferred range being about 20–40° C. Step 52 also works at a range of pH, from at least about pH 2 to about pH 10, with the preferred pH being about pH 7.

Then at 54, the crystals are separated from the solvent and thereafter dried by any suitable dryer (such as a spray dryer) a second time at 56. At step 54, the undissolved isoflavones are separated from the solvent, removing much of the undesired colors and flavors with the solvent. It is believed that, particularly when water is used as the solvent, the separated solvent may be enriched in saponins or the isoflavone daidzin. Thus, the separated solvent may be of utility in processes calling for saponins or daidzin. The resulting dried material is very light tan, bland tasting, and approximately 60–85% isoflavones on a solids basis.

The dry material appearing at step 56 (FIG. 5) may be used as an end product. Or, optionally, it may be circulated one or more times through a closed loop shown in FIG. 3 where the material is redissolved at step 43, concentrated to form crystals at step 45, the crystals and remaining liquid separated at step 42, and the resulting material redried at step 40. This process may be repeated, as desired. The end product at output 41 is approximately 70–90% solids.

In order to fine tune the characteristics of the product, the dry powder resulting from step 40 or 50 (FIG. 6) may have an additional, preferably dry, selected ingredient added thereto at 60. The dry powder and added ingredient are blended at 62 for use as a food ingredient or the like. The food ingredient may be any in a group including: soy flour, soy protein concentrate, soy protein isolate, soy fiber, fluid lecithin, granular lecithin, vegetable oil, phytosterols, phytosterol esters, stanols, stanolesters, tocopherols, d-alpha tocopherols, d, I-alpha tocopherols, tocotrienols, and mixtures thereof.

Food products which may incorporate the isoflavones produced by the invention may include: cereals, yogurt, margarine, health bars, tea and other beverages, and meal replacements.

Figure 6:
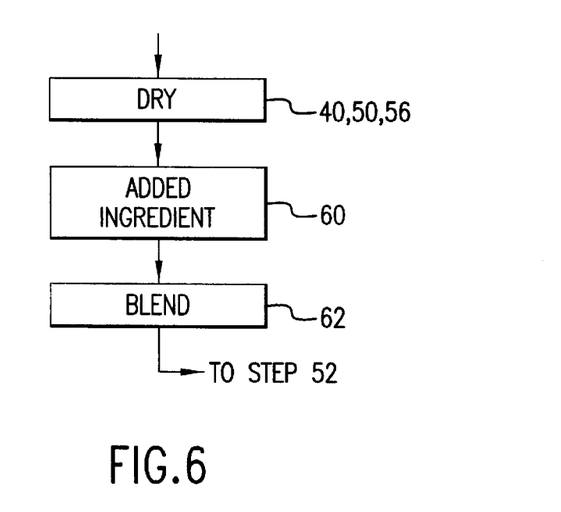
FIG. 6 is a fragment of FIG. 4 including a step of blending the inventive product with an added ingredient.

The advantages of the process of FIGS. 5 and 6 is that it permits storage, better blending, and closer control over the specifications of the final product so that quality control is easier. In addition, drying the product at 40 requires less energy and equipment usage since the reverse osmosis or ultrafiltering at 49 removes large amounts of water and since it is no longer necessary to have large batches of product sitting in large tanks for long periods of time during which crystals are formed and separated from their mother liquid.

Since the product may be held in storage in a dry form, there is less time for contamination to occur.

The dry product better enables a final usage in many forms such as pills, liquids, health bars, ingredients for various foods, and the like.

EXAMPLES

1) Ultrafiltration of Soy Solubles

Using a stainless steel steam-heated immersion coil, soy solubles (15.26 kg) were heated to a constant temperature of about 80° C. The soy solubles were then passed through a model 92-HFK-131-UYU spiral wound, polysulfone, 10,000 nominal molecular weight cut-off ultrafiltration membrane (Koch Membrane Systems, Inc., St. Charles, Ill.) by using a peristaltic pump. Back pressure on the exit side of the membrane was adjusted by means of a hand-tightened clamp to provide a permeate flow of 70 ml/minute. Ultrafiltration was continued until 9.4 kg of permeate was collected leaving 4.8 kg of retentate. Isoflavone profiles of the various fractions are shown below:

| Sample | Weight (kg) | T Solids | Total Isoflavones (g) | Genistin (g) | Daidzin (g) |
| --- | --- | --- | --- | --- | --- |
| Solubles | 15.26 | 8.65 | 11.45 | 4.01 | 4.30 |
| Retentate | 4.8 | 11.5 | 4.63 | 1.75 | 1.67 |
| Permeate | 9.4 | 7.7 | 6.6 | 2.29 | 2.68 |

2) Diafiltration of UF Retentate

Ultrafiltration retentate (80° C. initial temperature) was subjected to ultrafiltration as described in Example 1, except that 4.8 kg of tap water (25° C.) was fed into the retentate at a feed rate which is the same as the permeate rate or flux of the permeate that was being produced. The retentate was then further ultrafiltered to a final weight of 1.93 kg. Isoflavone profiles of the various fractions is shown below:

| Sample | Weight (kg) | % Solids (g) | Total Isoflavones (g) | Genistin (g) | Daidzin (g) |
| --- | --- | --- | --- | --- | --- |
| Retentate | 4.8 | 11.5 | 4.63 | 1.75 | 1.67 |
| Diafilt. Permeate | 7.25 | 4.28 | 2.12 | 0.72 | 0.96 |
| Diafilt. Retentate | 1.93 | 12.26 | 2.14 | 0.91 | 0.58 |

3) Adsorption and Recovery of Isoflavones From a Resin

A glass liquid-chromatography column (2.54 cm i.d.) was slurry packed in 70% ethanol with Dow XUS 40323 divinylbenzene, ethylvinylbenzene copolymer resin. The resin was cleaned with an additional 500 mL of 70% wt ethanol followed by 0.1% wt NaOH (500 mL) and water (500 mL). The resin was then back-flushed with water until the resin bed volume had expanded by about one half of its originally packed volume in order to partition the resin by size. The final packed volume was 100 mL. Fresh UF permeate (2000 mL or 20 column volumes) at an initial temperature of 60° C. was fed through the resin bed at 6 column volumes/hour or 10 mL/minute.

The resin bed was washed with 500 mL of water at 10 mL/minute to remove residual sugars and other impurities. Isoflavones were then eluted from the resin with a linear gradient of 20–95% ethanol (500 mL total) at 10 mL/minute. Next, the entire ethanolic isoflavone containing fraction was vacuum dried to obtain a product with the following profile:

| Sample | Weight (g) | Total Isoflavones (g) | Genistin (g) | Daidzin (g) |
|---|---|---|---|---|
| Column Product | 6.56 | 2.2 | 0.92 | 0.83 |

4) Elimination of Undesirable Taste and Color

The process described in U.S. Pat. No. 5,679,806 results in a product which is enriched in isoflavone fractions at a concentration of 30–50% on a dry basis. This product has a reddish-brown color and has bitter flavor. Although its high isoflavone content makes it a desirable product for many applications, its color and flavor may preclude its use in certain types of products where sensory attributes are important, such as foods and beverages.

This example produces a product which is lighter in color and bland in flavor, with a higher isoflavone concentration which occurs upon removal of the color and flavor components. The new product produced by this example also has an increased utility because smaller quantities of the starting material are required to deliver approximately the same amount of isoflavones. Also, the improvement in flavor and color enables a use of the isoflavones in a wide variety of applications, such as foods, beverages, medical foods, and certain dietary supplement products.

Soy solubles ultrafiltered at 22 produce a permeate having approximately 1–20% solids. This leads to a drying end step that may be carried out by any suitable means, the preferred means being spray drying.

More particularly, at 28, this permeate was passed through a liquid chromatography column containing a polystyrene divinyl-benzene resin ("Amberlite-XAD-4") to adsorb isoflavones. Thereafter, at 30, the resin was washed with water. Then, the isoflavones were eluted from the resin 32 with aqueous ethanol (in the range of 20–100% of alcohol and preferably about 70% ethanol). Next, the ethanol was evaporated at stage 38 to about 1.098% solids in order to produce a feed to a dryer at 38. In this example, the evaporator was heated by direct steam injection. While any of many types of dryers may be used, preferably a spray dryer is used at 40.

However, with this example, instead of completion of spray drying after elution step 32, the product was treated in the following manner:

19.29 kg of spray drier feed, containing a visible amount of precipitated material, was evaporated under vacuum in order to remove water and increase solids content. 200 g samples were taken both prior ("Spray Dryer Feed") and during ("Concentrate 1" and "Concentrate 2") evaporation in order to monitor the effect of solids content on the isoflavone recovery. These samples were allowed to cool to room temperature (about 20° C.) and subsequently centrifuged at 900×G for about 5 minutes in order to sediment the precipitate. The resulting supernatant was poured off of the sedimented precipitate and then the precipitate was dried at 140° F. (60° C.) for 16 hours. Next, all samples were analyzed for isoflavone content by HPLC, and were found to be a light cream color and to have a bland taste.

The recovery of isoflavones during the test carried out in this example are set forth in the following tables. Table 1 gives the isoflavone recovery during a processing of three samples designated A-C. The samples are designated A were taken from a spray-dryer feed, samples B (Concentrate I) were taken from the evaporator at step 38 during an early stage of the evaporation, and samples C (Concentrate II) were taken from the evaporator during a later stage of the evaporation. For each of the samples, the tests were run, respectively, on a complete dryer feedstream (A), upon a supernatant which was poured off after decanting (B), and upon the precipitate (C).

The solids prior to centrifugation and the amounts of isoflavones that were recovered are set forth in Table 2. The breakdown of the isoflavones that were recovered are set forth in Table 3. The conclusion is that each of the tests shows results that are attractive for certain uses. Therefore, the practitioner will select the particular process which best reflects the results that he seeks.

TABLE 1

| | Sample | % Solids (Soy Whey) | Isoflavones ppm | Weight (g) | Total Isoflavones |
|---|---|---|---|---|---|
| A | Spray Dryer Feed | 1.098 | 5583.4 | 200.04 | 1.117 |
| A | Spray Dryer Feed Supertant | 0.848 | 2937.6 | 192.04 | 0.564 |
| A | Dried Spray Dryer Feed Precipitate | 100.00 | 849624.8 | 0.56 | 0.477 |
| B | Concentrate I | 1.814 | 9313.5 | 200.01 | 1.863 |
| B | Concentrate I Supertant | 1.308 | 3980.8 | 185.35 | 0.738 |
| B | Dried Concentrate I Precipitate | 100.0 | 891696.8 | 1.21 | 1.077 |
| C | Concentrate II | 4.633 | 23404.6 | 200.00 | 4.681 |
| C | Concentrate II Supernatant | 3.173 | 8712.9 | 170.72 | 1.487 |
| C | Dried Concentrate II Precipitate | 100.0 | 838399.3 | 3.65 | 3.057 |

TABLE 2

| % Solids Prior to Centrifugation | % Recovery of Isoflavones in Centrifuged Precipitate |
|---|---|
| 1.098 (A) | 49.49 |
| 1.814 (B) | 60.39 |
| 4.633 (C) | 68.22 |

TABLE 3

| Isoflavone | Dried Spray Dryer Feed Precipitate (ppm) A | Dried Concentrate I Precipitate (ppm) B | Dried Concentrate II Precipitate (ppm) C |
|---|---|---|---|
| Daidzin | 347109.3187 | 422936.0742 | 412219.9703 |
| Glycitin | 37066.4070 | 43523.2763 | 44077.5906 |
| Genistin | 408166.8156 | 357561.8669 | 305240.8582 |
| Malonyl- | 4195.0096 | 6128.8092 | 7556.7644 |

TABLE 3-continued

| Isoflavone | Dried Spray Dryer Feed Precipitate (ppm) A | Dried Concentrate I Precipitate (ppm) B | Dried Concentrate II Precipitate (ppm) C |
|---|---|---|---|
| Daidzin Malonyl-Glycitin | 67.4223 | 96.0281 | 157.1695 |
| Acetyl-Daidzin | 26792.2537 | 32540.1269 | 35771.3900 |
| Acetyl-Glycitin | 389.8314 | 794.5519 | 1522.1046 |
| Malonyl-Genistin | 1755.5026 | 2469.0077 | 3581.2460 |
| Daidzein | 2952.0643 | 3814.0725 | 3615.3280 |
| Acetyl-Genistin | 18471.3792 | 19019.5539 | 21794.8883 |
| Glycitein | 1031.0817 | 1039.2615 | 1154.3133 |
| Genistein | 1627.7324 | 1774.1731 | 1707.7167 |
| Total ppm (%) | 849624.8 (85.0%) | 891696.8 (89.2%) | 838399.3 (83.8%) |

5) Soy Whey Starting Material

The staring material for these examples is soy whey. Soy whey is defined as a liquid from the isoelectric or the divalent cation precipitation of the solubilized fraction from the processing of soybeans into soyfoods.

A. Process Outline:

SOY WHEY (FIG. 3 at 20)→ULTRAFILTRATION (100,000 Mol. Wt. cut-off) (FIG. 3 at 22)→PERMEATE (FIG. 3 at 26)→REVERSE OSMOSIS (concentration) (FIG. 4 at 27)→ADSORPTIVE RESIN (FIG. 3 at 28)→WATER WASH RESIN (FIG. 3 at 30)→ELUTE PRODUCT WITH AQUEOUS ALCOHOL (FIG. 3 at 32) Adsorption and Recovery of Isoflavones From a Resin Utilizing Soy Whey As a Starting Material, Raw Material and End Product Description:

| Sample | Total Wt. (kg) | Total Isoflavones (g) | Isoflavone Conc. (%) |
|---|---|---|---|
| Reverse Osmosis Concentrate (ROC) | 882.49 | 219.74 | 0.0249 |
| Isoflavone Concentrate Product | 0.4223 | 155.17 | 36.744 |

A plurality of 1800 ml stainless steel liquid chromatography columns were slurry packed with "Amberlite" XAD-4 divinyl-benzene copolymeric polymeric adsorbent resin. The resin was cleaned repeatedly with 80% wt. ethanol, water and 0.1–0.3% wt. NaOH solution. The final bed volume (BV) of resin in each column was 1500 ml.

The reverse osmosis concentrate (ROC) was heated to a temperature of 80° C. Two columns (2×BV=BV2) were fed in series of 600 ml/min. and received a total of 36 liters (12 BV2) of ROC. Individual columns than received a 60° C. water wash at 100 ml/min. (3000 ml. or 2 BV) to remove residual sugars and other impurities. Isoflavones were then eluted from the washed columns with 60° C., 80% wt. ethanol at 90 ml/min. (5400 ml or 3.6 BV) producing an ethanolic isoflavone fraction. The ethanol was evaporated and removed from the isoflavone fraction. The isoflavone fraction was then spray dried, resulting in a total of 422.3 g of a 36.745% isoflavone powder.

B. Process Outline:

SOY WHEY (FIG. 3 at 20)→ULTRAFILTRATION (100,000 Mol. Wt. cut-off) (FIG. 3 at 22)→PERMEATE (FIG. 3 at 26)→REVERSE OSMOSIS (concentration) (FIG. 4 at 27)→ADSORPTIVE RESIN (FIG. 3 at 28)→WATER WASH RESIN (FIG. 3 at 30)→ELUTE PRODUCT WITH AQUEOUS ALCOHOL (FIG. 3 at 32)→EVAPORATE AQUEOUS ETHANOL (produce aqueous isoflavone solution) (FIG. 3 at 38)→AQUEOUS ISOFLAVONE SOLUTION UTILIZATION→
 1) DRY AQUEOUS ISOFLAVONE SOLUTION (FIG. 3 at 40)→PRODUCT#1, or
 2) COOL AQUEOUS ISOFLAVONE SOLUTION→CENTRIFUGE AQUEOUS ISOFLAVONE SOLUTION (isolate crystals) (FIG. 3 at 42)→DRY CRYSTALS (FIG. 3 at 40)→PRODUCT #2

C. Adsorption and Recovery of Isoflavones From a Resin Utilizing Soy Whey As a Starting Material.

Raw Material and End Product Descriptions:

| Sample | Total Wt. (kg) | Total Solids (%) | Total Isoflavones (g) | Isoflavone Conc. (%) |
|---|---|---|---|---|
| Reverse Osmosis Concentrate (ROC) from soy whey | 646.65 | 3.24 | 221.80 | 0.0343 |
| Isoflavone Fraction #1 | 7.73 | 4.62 | 72.03 | 0.9318 |

A plurality of 1800 ml stainless steel liquid chromatography columns were slurry with "Amberlite" XAD-4 divinyl-benzene copolymer adsorbent resin. The resin was cleaned repeatedly with 80% wt. ethanol, water and 0.1–0.3% wt. NaOH solution. The final bed volume (BV) of resin in each column was 1500 ml.

The reverse osmosis concentrate (ROC) was heated to a temperature of 80° C. Each column received 36 L (24BV) of ROC at 225 ml/min. Individual columns then received a 60° C. water wash at 100 ml/min. (4000 ml. or 2.7 BV) to remove residual sugars and other impurities. Isoflavones were then eluted from the washed columns with 60° C., 60% wt. ethanol at 90 ml/min. (7200 ml or 4.8 BV) producing an ethanolic isoflavone fraction. This sequence was repeated until a total of 654 L of ROC had been fed through the columns with the adsorbed isoflavones then recovered in the ethanolic fraction. The ethanol was evaporated and removed, producing isoflavone fraction #1. Fraction #1 had two possibilities for utilization: 1) drying fraction #1 to produce Product #1, or 2) to be used as a raw material to recover isoflavone crystals to produce a higher % wt. isoflavone, Product #2. Recovery Of Isoflavones From The Concentrated Column Effluent (Fraction #1):

The isoflavone fraction #1 was cooled over a 2 hour period to a temperature of 25° C. resulting in isoflavone crystal formation. A sample of the cooled isoflavone fraction #1 was then centrifuged at 900×G for 10 min. to pellet the isoflavone crystals. Next, the supernatant was poured off. The remaining pellets were vacuum dried (140° F., 16 hours) and analyzed for isoflavone content. Further purification of the pellets can be obtained by water washing and repeated centrifugation.

| Sample | Weight (g) | Total Isoflavones (g) | Isoflavones (%) |
|---|---|---|---|
| Isoflavone Product #1 (Isoflavone fraction #1 on a dry weight basis) | 357.13 | 72.03 | 20.2 |
| Isoflavone Product #2 | 3.02 | 2.05 | 67.9 |

The process that is described herein has the advantage of utilizing another common soy processing by-product, soy whey, as a starting material for the manufacture of isoflavone concentrates. When soy whey is used as the starting material, products produced from drying the concentrate column effluent can be approximately 20–40% wt., and preferably in the upper part of the range or 35–40% wt. isoflavone fractions. These products are reddish-brown in color and bitter in flavor. The high isoflavone content makes it useful for applications such as tableting and inclusion into some foods. However, where sensory attributes are important, further processing of the concentrated column effluent material can be done to produce isoflavone concentrate more suited to food and beverage additions.

Concentrated column effluents from the processing of soy whey and soy molasses can be centrifuged or filtered and then dried to produce a new isoflavone concentrate product. The new product is lighter in color, has a less bitter taste and is higher in isoflavone concentration. These improvements allow for a wider range of uses of soy whey and molasses in foods, beverages, medical foods and dietary supplements where sensory attributes are more of a concern.

6) Improved Recovery Of Isoflavones From A Dried Impure Product

This example produces a solid product that is lighter in color and bland in flavor with a higher isoflavone concentration that occurs upon removal of the color and flavor components than that produced by the process described in U.S. Pat. No. 5,679,806. The new product produced by this example also has an increased utility because it is possible to increase the concentration of isoflavones and, therefore, smaller quantities are required to deliver approximately the same amount of isoflavones. Also, the improvement in flavor and color enables a use of the isoflavones in a wider variety of applications, such as foods, food ingredients, beverages, medical foods, health bars, and certain dietary supplement products.

Another advantage of this process comes from the production of a readily water-soluble supernatant or filtrate fraction, which is different in isoflavone profile from the solid product. This product has an isoflavone ratio with proportionally higher levels of daidzin than the solid product, which solid product has a ratio that favors genistin. This water-soluble fraction is also expected to contain saponins. This water-soluble fraction can be further treated or used in applications where a higher level of water-solubility and/or daidzin or saponins may be desired.

The 30–50% spray dried product produced as described in U.S. Pat. No. 5,679,806 is the starting material for this process. Different lots of commercially produced spray-dried product were slurried with water. Slurried solutions were then filtered or centrifuged with or without adjusting the pH in the solutions so as to result in a solid product and the filtrate or supernatant. The separated fractions (the solid product and the filtrate or supernatant) were then dried and evaluated for isoflavone concentration. Laboratory parameters were also applied on a pilot-scale to test commercial feasibility of the process in producing the two fractions.

A. Three samples were prepared from Lot A (Feed is Spray Dried Product), as seen in Table 4 and as follows:

Three 10 g samples of Feed were weighed, then diluted with deionized water (70° C.) at the following three ratios (weight of Feed:weight of water): 1:2 (20 ml), 1:4 (40 ml) and 1:6 (60 ml).

Samples were mixed to dispersion and immediately filtered through an 11 micron, 6% open area filter cloth on a buchner funnel, into flask, under vacuum (20"Hg).

Filter cakes and filtrates were recovered, weighed and vacuum dried (24"Hg) at 70° C. for 16 hrs.

Dried samples were weighed, ground and then analyzed for isoflavone content.

The procedure was repeated utilizing a 5 micron, 2% open area filter cloth.

The results are reported in Table 4, and show that the cake is much enriched for isoflavones. The greatest degree of enrichment is seen at the higher dilutions, regardless of the size of the filter.

B. Two samples were prepared from Lot B (Feed is Spray Dried Product, Table 4) as follows:

100 g Feed weighed into 200 g of deionized water (20° C.) at a ratio of 1:2 and mixed to dispersion (approximately 30 min.).

Another sample was prepared by weighing 50 g Feed into 500 g of deionized water (20° C.) at a ratio 1:10 and mixed to dispersion (approximately 30 min.).

The pH of each sample was found to be about 4.0 and then a weighed aliquot of each dispersed sample was centrifuged at 2000 rpm for 5 min.

Each centrifuged sample was then split into two weighed portions of supernatant and pellet.

After dispensing the first aliquot, the 1:2 and 1:10 dispersions were both adjusted to a pH of approximately 9.0 with 50% Sodium Hydroxide.

Weighed aliquots were centrifuged at 2000 rpm for 5 min.

Each centrifuged sample was then split into two weighed portions of supernatant and pellet.

Samples were then dried under vacuum (24"Hg) at 70° C. for at least 16 hrs.

This procedure was repeated for both dilutions (ratio 1:2 and 1:10) with a water temperature of 70° C., and all else held constant.

The results are reported in Table 4, and show that the cake is much enriched for isoflavones. As with Example A, a greater enrichment is generally seen at the higher dilutions—especially at the higher pH. Increased temperature moderately increases isoflavone enrichment.

C. Large scale testing of the filtration procedure was done utilizing a pilot-scale rotary vacuum filter (RVF).

Rotary vacuum drum was fitted with an 11 micron, 6% open area filter cloth.

2.0 kg of Lot C (Feed is Spray Dried Product, Table 4) was dispersed into a total of 10 kg, 20° C. tap water (ratio 1:5) with a total mix time of 60 min.

The mixed sample was fed to the trough below the rotary vacuum drum to a steady level which maintained surface contact with the bottom of the drum.

The vacuum pulled sample onto the moving drum with the filter cloth, building up a layer of isoflavones.

A portion of the isoflavone layer was then cut off as the barrel rotated around at a rate of 0.8–1.0 rpm.

Vacuum to barrel at start of test was 6"Hg and steadied to 16"Hg for duration of filtration test.

Process produced two distinct products: cake and filtrate.

Samples were freeze dried prior to isoflavone analysis.

As seen in Example C of Table 4, the cake is much enriched for isoflavones at the pilot-scale level of treatment.

TABLE 4

Isoflavone Concentrate From Reconstituted Spray Dried Product

| Ex. | Dilution feed:water | % T.S. | Test | Condition water temp. | pH | Feed % isoflavone | Cake/Pellet % isoflavone | Super/Filtrate % isoflavone |
|---|---|---|---|---|---|---|---|---|
| A | 1:2 | 33.33 | Filter or Centrifuge 11 micron 6% open area | 70° C. | not adjusted | 47.66 Lot A | 75.06 | 31.35 |
|   | 1:4 | 20 |   |   |   |   | 81.58 | 31.84 |
|   | 1:6 | 14.3 |   |   |   |   | 85.3 | 31.8 |
|   | 1:2 | 33.33 | 5 micron 2% open area |   |   |   | 79.3 | 30.24 |
|   | 1:4 | 20 |   |   |   |   | 82.51 | 27.58 |
|   | 1:6 | 14.3 |   |   |   |   | 83.92 | 31.63 |
| B | 1:2 | 33.33 | 5 min. at 2000 rpm | 20° C. | 4.56 9 4.16 8.92 | 38.71 Lot B | 62.18 64.99 | 29.45 28.72 |
|   |   |   |   | 70° C. | 4.35 8.99 |   | 69.87 65.22 | 26.66 25.77 |
|   | 1:10 | 9.09 |   | 20° C. | 4.15 8.97 |   | 60.43 83.92 | 26.06 25.95 |
|   |   |   |   | 70° C. |   |   | 68.06 83.78 | 27.29 25.8 |
| C | 1:5 | 16.7 | RVF 11 micron 6% open area | 20° C. tap water | not adjusted | 50.14 Lot C | 82.8 | 26.7 |

Those who are skilled in the art will readily perceive how to modify the invention. Therefore, the appended claims are to be construed to cover all equivalent structures which fall within the true scope and spirit of the invention.

The claimed invention is:

1. A process for separating isoflavone fractions in an aqueous vegetable starting material, said process comprising the steps of:
   (a) heating an aqueous vegetable starting material to a constant temperature selected on a basis of an aqueous solubility of at least a desired isoflavone fraction that is selected to be recovered;
   (b) passing the heated starting material of step (a) through a treatment by an adsorptive material;
   (c) washing the adsorptive material of step (b) and eluting said at least a desired isoflavone fraction from the water-washed adsorptive material of step (b) with aqueous alcohol to form a stream;
   (d) at least partially removing the aqueous alcohol from the stream formed during the elution of step (c) in order to promote the crystallization of said at least a desired isoflavone fraction;
   (e) treating the eluted stream of step (d) to at least one treatment selected from a group consisting of ultrafiltration and reverse osmosis in order to produce a stream with a higher content of isoflavone solids; and
   (f) drying the higher solids stream of step (e) to form dry particles.

2. The process of claim 1 and the further step of adding a solvent to the dried particles of step (f) to form a second stream; and separating the crystallized at least one isoflavone fraction from the second stream formed by adding solvent in order to provide an output product.

3. The process of claim 2 and the further step of redrying said second stream before providing said output product.

4. The process of claim 1 wherein the treatment of step (e) is ultrafiltration.

5. The process of claim 1 wherein the treatment of step (e) is reverse osmosis.

6. The process of claim 1 wherein the treatment of step (e) is both ultrafiltration and reverse osmosis.

7. The process of claim 2, wherein the added solvent is selected from the group consisting of water, ethanol, isopropanol, methanol, and combinations of these solvents.

8. The process of claim 1, wherein the separated crystallized isoflavone fraction is blended with a food or food ingredient.

9. The process of claim 8, wherein the food ingredient is selected from the group consisting of sweeteners, soy flour, soy protein concentrate, soy protein isolate, soy fiber, fluid lecithin, granular lecithin, vegetable oil, phytosterols, phytosterol esters, stanols, stanolesters, tocopherols, d-alpha tocopherols, d, I-alpha tocopherols, tocotrienols, and mixtures thereof.

10. The process of claim 8 wherein said food ingredient is used in a food product selected from a group consisting of cereal, yogurt, margarine, health bars, tea, other beverages, and meal replacements.

11. The process of claim 2, wherein the solvent of step (e) is at a temperature between about 4° C. and 95° C.

12. The process of claim 11, wherein the solvent is at a temperature between about 20° C. and 40° C.

13. The process of claim 2, wherein the solvent is at a pH between about 2 and 10.

14. The process of claim 13, wherein the solvent is at a pH between about 6 and 8.

15. The process of claim 2 wherein the crystal separating step includes a process selected from a group consisting of decanting, hydrocloning, centrifuging and filtering.

16. The process of claim 2 wherein said separation step comprises the step of centrifuging the second stream formed by the added solvent.

17. The process of claim 1 and the added step providing a closed loop of steps following said step (f), said closed loop comprising the further steps of redissolving said dry particles of step (f), concentrating the redissolved particles in order to recrystallize said desired isoflavone fractions, separating said crystals of said redissolved particles from remaining liquid, and redrying said separated crystallized isoflavones.

18. The process of claim 17 and the further step of recirculating said redried crystallized isoflavones through said closed loop until a desired concentration of isoflavones is reached.

19. A process of separating at least two isoflavone fractions in an aqueous vegetable starting material, said process comprising the steps of:

(a) heating an aqueous vegetable starting material to a constant temperature selected on a basis of an aqueous solubility for at least one desired isoflavone fraction that is to be recovered;

(b) passing the starting material of step (a) through an ultrafiltration membrane to obtain a permeate, the membrane having a cut-off which passes said desired isoflavone fraction;

(c) treating the permeate with an adsorptive material and thereafter eluting said desired isoflavone fraction;

(d) treating the eluted stream of step (c) with at least one treatment selected from the group consisting of passing the stream through an ultrafiltration membrane or a reverse osmosis system, said treatment increasing the solids through basis of said desired isoflavones fraction; and (e) drying the desired isoflavone fraction of step (d) to a powdered state.

20. The process of claim 19 and the further step of adding and blending a selected amount said isoflavone fraction in order to bring said isoflavone fraction to a predetermined characteristic specification.

21. The process of claim 19 wherein the treatment of step (d) is ultrafiltration.

22. The process of claim 19 wherein the treatment of step (d) is reverse osmosis.

23. The process of either claim 1 or 19 wherein there are a plurality of isoflavone fractions recovered in both said heating step and after said treatment of said isoflavone fraction by ultrafiltration or reverse osmosis.

24. The process of either claim 1 or 19 wherein the process of step (c) is a continuous process further comprising the sub-steps of:

providing a plurality of liquid chromatography columns, each of which is filled with an adsorptive resin arranging the columns so that at least one of said plurality of columns is used for treating the permeate while at least one other of said plurality of columns is eluting; and switching between the columns so that said at least one of said plurality of columns is washing while said at least one other of said plurality of columns is eluting.

25. The process of either claim 1 or 19 wherein said adsorptive material is a styrene divinyl-benzene copolymer.

26. The process of either claim 1 or 19 wherein said adsorptive material of step (c) is selected from a group consisting of ethylvinylbenzene-divinyl-benzene, styrene-divinyl-benzene copolymers and polystyrene polymers.

27. A process for the production of a selected group of isoflavone fractions from vegetable matter, said process comprising the steps of:

(a) obtaining a starting material by heating an aqueous water soluble vegetable material feed stream containing a compound selected from a group consisting of soy molasses and soy whey, said heat being a temperature selected to solubilize a plurality of isoflavone fractions in said stream;

(b) ultrafiltering the stream resulting from step (a), said filtration being carried out by a membrane having a cut-off which produces a permeate containing said plurality of isoflavone fractions solubilized in step (a);

(c) sending said permeate through an adsorbing resin, eluting with an eluant therefrom an eluted stream, and driving off the eluant to form a stream which is approximately 1–20% solids; and (d) treating the eluted stream of step (c) with at least one additional treatment selected from the group consisting of ultrafiltration or a reverse osmosis system.

28. The process of claim 27 and the added steps of drying the treated stream of step (d) to a dried powder state; adding a solvent to the dried powder in order to dissolve impurities; and separating the impurities and solvent from the plurality of isoflavone fractions.

29. The process of claim 27 and the added steps of drying material in the stream treated in step (d), redissolving said dried material, concentrating the redissolved material to crystallize the isoflavones, separating the crystallized redissolved material from remaining liquid, and redrying the separated redissolved material.

30. The process of claim 29 and the further step of repeating said added steps until said isoflavones reach a desired level of highly concentrated isoflavones.

31. The process of claim 28 and the further steps of selecting an amount of isoflavone to bring said dried powder to a predetermined characteristic specification; and blending said dried powder with a selected amount of isoflavones that are separated from said impurities.

32. The process of claim 27 wherein said ultrafiltration of both steps (b) and (d) uses membranes having a nominal molecular weight cut-off range of about 600–1,000,000.

33. The process of claim 27 wherein said ultrafiltration of both steps (b) and (d) uses membranes having a nominal molecular weight cut-off range of 100,000 nominal molecular weight.

34. The process of claim 27 wherein said adsorbing process of step (c) is a continuous process using a plurality of liquid chromatography columns wherein at least one of said plurality of liquid chromatography columns is loading while another of said at least one of said columns is washing and while still another of said at least one of said columns is eluting.

35. The process of claim 27 wherein said stream of step (d) is cooled to approximately 4 to 45° C. and is subjected centrifugation at about 900×g.

36. The process of claim 27 wherein said vegetable matter is soy.

37. The process of any one of the claims 1, 19 and 27 and the further steps of forming said dry powder into a product selected from a group consisting of pills, liquids, food ingredients, health bars, cereals, yogurt, margarine, tea, beverages, meat replacements, medical foods, or dietary supplements.

38. A process for production of a selected group of at least two isoflavones comprising:

(a) heating an aqueous feed stream of water soluble vegetable matter containing a plurality of isoflavone fractions, said heat being a temperature selected to solubilize a plurality of selected isoflavone fractions in said feed stream;

(b) ultrafiltering said feed stream of step (a) by use of a membrane having a cut-off which produces a permeate containing said selected isoflavone fractions solubilized in step (a);

(c) sending said permeate of step (b) to move through an adsorbing resin to form an eluted stream which is about 1–20% solids;

(d) evaporating said eluted stream of step (c) and (e) providing a closed loop for processing said evaporated stream of step (d), said closed loop comprising the further steps of:

(e1) drying said stream of step (e) to produce particles;

(e2) redissolving said dried particles;

(e3) concentrating said redissolved particles of step (e2) to crystallize said selected isoflavone fractions;
(e4) separating the crystals of step (e3) from remaining liquid; and
(e5) redrying said separated crystals of step (e4).

39. The process of claim 38 and the further step of recirculating said redried crystals through said closed loop until a desired concentration of isoflavones is achieved.

* * * * *